United States Patent [19]

Wu et al.

[11] Patent Number: 5,279,751
[45] Date of Patent: Jan. 18, 1994

[54] REACTION PRODUCTS OF SULFUR-CONTAINING DIACYL HALIDES WITH PHOSPHORODITHIOIC ACID AND PHENOLS OR THIAZOLES AS MULTIFUNCTIONAL LUBRICANT ADDITIVES

[75] Inventors: Shi-Ming Wu, Newtown, Pa.; Andrew G. Horodysky, Cherry Hill, N.J.

[73] Assignee: Mobil Oil Corporation, Fairfax, Va.

[21] Appl. No.: 806,970

[22] Filed: Dec. 12, 1991

Related U.S. Application Data

[63] Continuation-in-part of Ser. No. 590,882.

[51] Int. Cl.$^5$ .................................... C10M 137/00
[52] U.S. Cl. ............................ 252/46.6; 252/46.7; 252/400.21; 252/400.22; 558/153
[58] Field of Search ............... 252/46.6, 46.7, 400.21, 252/400.22; 562/842, 9; 560/195; 558/153

[56] References Cited

U.S. PATENT DOCUMENTS

| | | | |
|---|---|---|---|
| 3,361,671 | 1/1968 | Lowe | 252/46.7 |
| 3,456,039 | 7/1969 | Beriger | 558/153 |

FOREIGN PATENT DOCUMENTS

| | | |
|---|---|---|
| 0527419 | 7/1956 | Canada . |
| 0839924 | 6/1960 | United Kingdom . |

*Primary Examiner*—Margaret Medley
*Attorney, Agent, or Firm*—Alexander J. McKillop; Malcolm D. Keen; Howard M. Flournoy

[57] ABSTRACT

Reaction products of sulfur-containing diacyl halides with phosphorodithioic acids and phenols or thiazoles are effective EP/antiwear and antioxidant additives for lubricants.

32 Claims, No Drawings

REACTION PRODUCTS OF SULFUR-CONTAINING DIACYL HALIDES WITH PHOSPHORODITHIOIC ACID AND PHENOLS OR THIAZOLES AS MULTIFUNCTIONAL LUBRICANT ADDITIVES

CROSS-REFERENCE TO RELATED APPLICATIONS

This application is a continuation-in-part of application Ser. No. 07/590,882, filed Oct. 1, 1990, now abandoned.

BACKGROUND OF THE INVENTION

This application is directed to novel reaction products of sulfur-containing diacyl generating halides, e.g., diacyl halides with phosphorodithioic acids and phenols or thiazoles which function as multifaceted additives when incorporated into lubricants and to lubricant compositions containing same.

Lubricants, scch as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode. Additionally, severe oxidation leads to a loss of lubrication properties, and in especially severe cases this may cause complete breakdown of the device being lubricated. Many additives have been tried, however, many of them are only marginally effective except at high concentrations. Improved antioxidants are clearly needed.

Antioxidants or oxidation inhibitors are used to minimize the effect of oil deterioration that occurs when hot oil is contacted with air. The degree and rate of oxidation will depend on temperature, air and oil flow rates and, of particular importance, on the presence of metals that may catalytically promote oxidation. Antioxidants generally function by prevention of chain peroxide reaction and/or metal catalyst deactivation. They prevent the formation of acid sludges, darkening of the oil and increases in viscosity due to the formation of polymeric materials. Additionally lubricants are under heavy stress that can affect their extreme pressure/antiwear and load carrying ability particularly between steel on steel moving surfaces.

The use of phosphorus compound per se as load-carrying or EP additives in lubricant compositions is well known. Also, the use of sulfur-containing compounds in lubricant compositions is well known. However the instant combination of sulfur, phosphorus and phenol or thiazole containing additives to the best of applicants' knowledge was heretofore unknown.

It is an object of this application to provide lubricant compositions having enhanced oxidative stability, reduced wear, increased load carrying/EP capabilities and improved lubricity.

SUMMARY OF THE INVENTION

This invention is directed to the use of reaction products of sulfur-containing diacyl halides or other diacyl generating species with phosphorodithioic acids and phenols or thiazoles as multifunctional additives, their use in lubricant compositions containing such additives to improve their performance properties, to the reaction products per se and to lubricant compositions containing same.

DESCRIPTION OF PREFERRED EMBODIMENTS

Sulfur-containing diacyl halides, e.g., chlorides, or other suitable diacyl generating species can be prepared from sulfur-containing aliphatic dicarboxylic acids and/or diesters with inorganic acid halides. In general, sulfur-containing terminal dicarboxylic acids/diesters are preferably reacted withsuch as thionyl chloride. However, the invention is not limited to thionyl chloride as the inorganic acid halide. The inorganic acid halide can be thionyl bromide, iodide or fluoride. other inorganic acid halides such as $PCl_3$, $PBr_3$ or $PCl_5$ may be used as well. Diacyl halides in general are suitable as the core moiety to couple with phosphorodithioic acids, phenols and/or thiazoles.

The sulfur-containing diacyl halides can also be prepared from aromatic sulfur-containing dicarboxylic acids and/or diesters if so desired. However, sulfur-containing aliphatic dicarboxylic acids are preferred. The aliphatic moiety generally contains at least 6 to 8 carbon atoms or more. Preferred acids include 3, 3'-thiodipropionic acid and the like. The sulfur-containing diacyl halides useful herein have the following generalized formula:

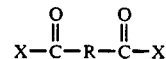

where X is halide, e.g., fluoride, chloride, bromide or iodide, preferably chloride. R is sulfur-containing and preferably aliphatic having from 0 to about 80 carbon atoms, preferably from 4 to about 32 carbon atoms and optionally containing oxygen or nitrogen or mixtures thereof.

Dihydrocarbyl phosphorodithioic acids can be prepared in a variety of ways; e.g., from the reaction of alcohols/phenols or amines with phosphorus pentasulfide. Alcohols can include primary (1°) and secondary (2°) alkanols or mixed alkanols as well as phenols or mixtures thereof. Preferred are alcohols such as 2-ethyl-1-heptanol. Amines can include primary (1°) and secondary (2°) aliphatic or aromatic amines or mixed alkyl-aryl amines, aryl-alkyl amines, alkoxylated and/or polyalkoxylated amines or the like. Preferred are amines such as bis(2-ethylhexyl) amine.

The incorporation of dihydrocarbyl phosphorodithioic acids and phenols or thiazoles onto the backbone of sulfur-containing diacyl halides provides the basis for the unique internal synergistic extreme pressure/antiwear, antioxidant activity and enhanced lubricity.

Any suitable phenol or thiazole or mixture of phenols and thiazoles known in the art may be used herein. For example, mono-alkylated phenols such as nonylphenol or dialkylated phenols are highly suitable for use herein. Also usefull are alkoxyphenols, biphenols, sulfurized phenols and sulfurized alkylphenols.

Suitable thiazoles include but are not limited to, for example, 2-mercaptobenzothiazole; 2,5-dimercapto-1, 3, 4-thiazole; 2-benzothiazole; 2-aminothiazole, 2-aminobenzothiazole and the like.

Suitable phosphorodithioic acids may be made as indicated above and include but are not limited to bis(2-ethylhexyl)phosphorodithioic acid and bis(ethylhexylamido)phosphorodithioic acid, and the like.

The additives in accordance with the invention are readily prepared by reacting sulfur-containing diacyl halides derived from sulfur-containing dicarboxylic acids with dihydrocarbyl phosphorodithioic acids and phenols or thiazoles. Generally speaking (1) an acid, such as 3, 3'-thiodipropionic acid is reacted in molar ratios varying from about 3:1 to 1:3 moles preferably 1:1 to 1:1.5 moles of acid to halogenating agent such as $SOCl_2$ or $SOBr_2$ under ambient or autogenous pressure at temperatures varying from about 0° C. to about 120° C. until the diacyl halide is obtained and (2) reacting the diacyl halide with an equimolar ratio phosphorodithioic acid and thiazole or phenol to obtain the desired additive product. However, up to 200% excess of phosphorodithioic acid and/or thiazole or phenol can be used or less than molar amounts often as little as 20% of stoichiometric amounts of phosphorodithioic acid and/or thiazole or phenol may be used. Accordingly, molar, less than molar or more than molar ratios of the various reactants may be used.

A solvent may be used if desired. Any suitable hydrocarbon solvent such as toluene, benzene, xylene, cyclohexane, and the like may be used. The temperature of reaction will depend upon the solvent used, if any. Step two, however, will generally be run at the temperature of reflux. The temperature, however, is not believed to be critical and can vary over a wide range of from about 10° to about 225° C. Times of reaction are not critical, but they will vary depending upon the size and complexity of the reactants. Under normal conditions, the reaction with the contemplated reactants can be completed in from about one hour to about ten hours, preferably from about two hours to about six hours under ambient or autogenous pressure.

Other additives, such as detergents, dispersants, antioxidants, antiwear agents, extreme pressure additives, pour depressants, antirust additives and the like may be present in the composition. These can include phenates, sulfonates, polymeric succinimides, zinc dialkyl or aryl dithiophosphates, polymers, calcium and magnesium salts, polymeric viscosity index improving additives such as olefin copolymers, sulfurized olefins and the like.

The compounds of the invention are used with lubricating oils or greases to the extent of from about 0.01% to about 10% by weigh of the total composition, preferably from about 0.2% to about 3%.

The lubricants contemplated for use with the novel additives herein disclosed include mineral and synthetic hydrocarbon oils of lubricating viscosity, mixtures of mineral oils and synthetic oils and greases from any of these, including the mixtures. The synthetic hydrocarbon oils include long chain alkanes such as cetanes and olefin polymers such as oligomers of hexane, octene, decene and dodecene, etc. These vicinal diol-derived phosphites are especially effective in synthetic oils formulated using mixtures of synthetic hydrocarbon olefin oligomers and lesser amounts of hydrocarbyl carboxylate ester fluids. The other synthetic oils, which can be used alone with the phosphorus compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty minerals having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salt and soaps of low-, intermediate- and high-molecular weight acids and of nut oil acids.

Clays which are useful as starting materials in forming thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolie, biotite, vermiculite, zeolite clays, and the like. The thickening agent is employed in an amount from about 0.5 to about 30, and preferably from 3 to about 15 percent by weight of the total grease composition.

The following examples typify but are not meant in any way to limit the scope of the invention.

EXAMPLE 1a

Approximately 780 g of 2-ethyl-1-hexanol was stirred in a reactor equipped with a condenser, thermometer, nitrogen purge inlet and outlet to a caustic trap, to which phosphorus pentasulfide was introduced in portions (6 ×55.5 g), while the reaction temperature was maintained at approximately 90° C. and reacted for six additional hours. It yielded 1052 g of bis(2-ethylhexyl)-phosphorodithioic acid upon filtration.

EXAMPLE 1b

Under the same reaction conditions as described in Example 1a, approximately 483 g of bis(2-ethylhexyl)amine was reacted with phosphorus pentasulfide in portions (3×37 g), while the reaction temperature was maintained at approximately 90° C. and then heated up to 120° C. for six additional hours. It provided 590 g of bis(2-ethylhexylamido) phosphorodithioic acid.

EXAMPLE 2

Approximately 35.6 g of 3,3'-thiodipropionic acid and 150 ml of toluene were charged to a stirred reactor equipped with a condenser, thermometer, and nitrogen sparger. A solution of thionyl chloride (54.6 g) in 50 ml of toluene was added dropwise to the reactor, while the reaction temperature was kept under 70° C. The mixture was then heated to 80° C. for one hour. A mixture of bis(2-ethylhexyl) phosphorodithioic acid (70.8 g from Example 1a) and 2-mercaptobenzothiazole (33.4 g) in 100 ml of toluene was then introduced slowly over a period of 15 minutes. The reactive mixture was heated to reflux for an additional six hours. The resulting mixture was filtered and evaporated under reduced pressure at 130° C. to yield 101 g of dark brown fluid.

EXAMPLE 3

Under the same reaction conditions as generally described in Example 2, approximately 35.6 g of 3,3'-thiodipropionic acid in 150 ml of toluene was reacted with thionyl chloride (59.5 g) in 50 ml of toluene. A mixture of bis(2-ethylhexyl) phosphorodithioic acid (70.8 g) and nonylphenol (44 g) in 100 ml of toluene was then introduced. The final product was 147 g of dark brown fluid.

EXAMPLE 4

The procedure of Example 2 was modified as follows. After the diacyl chloride was generated, a mixture of bis(2-ethylhexylamido) phosphorodithioic acid (71 g from Example 1B) and nonylphenol (44 g) in 100 ml of toluene was introduced and stirred at 90° C. for six hours. The mixture was evaporated under reduced pressure at 130° C. to yield 154 g of dark brown fluid.

Reaction products of diacyl halides with phosphorodithioic acids and phenols or thiazoles exhibit outstanding performance as multifunctional antioxidant (Table 1) and antiwear (Table 2) lubricant additives.

Evaluation of Products

The product of the examples were evaluated using the *Catalytic Oxidation Test* as shown in Table 1 below. The results demonstrate the remarkable antioxidant features of the examples with respect to control of the increase in viscosity and acidity. The Catalytic Oxidation Test may be summarized as follows: Basically the lubricant is subjected to a stream of air which is bubbled through the oil formulation at the rate of five liters per hour at 325° F. for 40 hours. Present in the composition are samples of metals commonly used in engine construction, namely iron, copper, aluminum and lead, see U.S. Pat. No. 3,682,980 incorporated herein by reference for further details.

TABLE 1

| | Catalytic Oxidation Test 325° F., 40 Hours | |
|---|---|---|
| Item | Increase In Acidity Change in Acid Number Δ TAN | Viscosity Increase Percent Change in Viscosity Δ KV |
| Base Oil (100% Solvent Paraffinic Neutral Mineral Oil) | 16.48 | 140.3 |
| 1% of Example 2 (In base oil) | 3.27 | 21.8 |
| 1% of Example 3 (In base oil) | 2.19 | 25.2 |
| 1% Of Example 4 (In base oil) | 0.41 | 11.9 |

The Catalytic Oxidation Test results confirm the excellent control in both acidity and viscosity increase. These additives demonstrate remarkable antioxidant properties at only 1% concentration levels.

The antiwear properties of the examples were also evaluated using the *Four Ball Wear Test* as shown in Table 2. The results clearly exhibit the excellent antiwear properties inherent in these unique compositions.

In the Four Ball Test three stationary balls are placed in a lubricant cup and a lubricant containing the compound to be tested is added thereto, and a fourth ball is placed in a chuck mounted on a device which can be used to spin the ball at known speeds and loads. The examples were tested using half inch stainless steel balls of 5200 steel for thirty minutes under 60 kg load at 2000 rpm and 200° F. If additional information is desired cnosult test method ASTM D2266 and/or U.S. Pat. No. 4,761,482.

TABLE 2

| Four-Ball Wear Test 60 Kg, 200° F., 2000 rpm, 30 min. | |
|---|---|
| Item | Wear Scar Diameter (mm) |
| Base Oil (80% Solvent Paraffinic Bright, 20% Solvent Paraffinic Neutral Mineral Oils | 3.33 |
| 1% of Example 2 (In base oil) | 0.84 |
| 1% of Example 3 (In base oil) | 0.54 |
| 1% of Example 4 (In base oil) | 0.52 |

The Four-Ball Wear Test results again demonstrate the excellent antiwear properties of these compositions when used at only 1% concentration in mixed mineral oils.

Reaction products of sulfur-containing diacyl halides in accordance with the invention exhibit outstanding performance as multifunctional antioxidant (Table 1) and antiwear (Table 2) lubricant additives in fully formulated lubricants oils.

Accordingly, the use of additive concentrations of reaction products in the above-mentioned compositions in premium quality industrial, automotive and marine lubricants will provide multifunctional EP/antiwear-/antioxidant properties.

The invention and its broader aspects is not limited to the specific details shown and described. Although the invention has been described with preferred embodiments, it is to be understood that modifications and variations may be made without departing from the spirit and scope of the invention as those skilled in the art will readily understand.

What is claimed is:

1. An improved lubricant composition comprising a major amount of an oil of lubricating viscosity or a grease prepared therefrom and a minor amount of a multifunctional antioxidant, antiwear, load carrying or extreme pressure additive product prepared by reacting (1) a sulfur-containing diacyl or mixture thereof having the formula

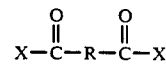

wherein R is sulfur-containing having up to 80 carbon atoms and optionally containing oxygen or nitrogen or mixtures thereof and X is halide selected from the group consisting of bromide, chloride, fluoride and iodide with (2) a phosphorodithioic acid and (3) a phenol or a thiazole or mixtures thereof at temperatures varying from 10° to about 225° C. in equimolar, more than equimolar or less than equimolar ratios of said diacyl to said phosphorodithioic acid under ambient or autogenous pressure for times of from about 1 to 10 hours.

2. The composition of claim 1 wherein X is chloride.

3. The composition of claim 1 wherein the sulfur-containing diacyl halide is derived from a sulfur-containing dicarboxylic acid and thionyl chloride.

4. The composition of claim 3 wherein said thiazole is selected from the group consisting of 2-mercaptobenzothiazole; 2,5-dimercapto-1,3,4-thiazole; 2-aminothiazole and 2-aminobenzothiazole or mixtures thereof.

5. The composition of claim 4 wherein said thiazole is 2-mercaptobenzothiazole.

6. The composition of claim 1 wherein said phenl is selected from the group consisting of monoalkyl phenols, dialkylphenols, alkoxyphenols, sulfurized alkyl phenols and sulfurized dialkyl phenols or mixtures thereof.

7. The composition of claim 6 wherein said phenol is nonylphenol.

8. The composition of claim 1 wherein the reactants are (1) 3,3'-thiodipropionic acid and thionyl chloride, (2) bis(2-ethylhexylamido) phosphorodithioic acid and (3) nonylphenol.

9. The composition of claim 1 wherein the the reactants are (1) 3,3'-thiodipropionic acid and thionyl chloride (2) bis(2-ethylhexyl) phosphorodithioic acid and (3) 2-mercaptobenzothiazole.

10. The composition of claim 1 wherein the reactants are (1) 3, 3'-thiodipropionic acid and thionyl chloride, (2) bis(2-ethylhexyl) phosphorodithioic acid and (3) nonylphenol.

11. The composition of claim 1 wherein the lubricant is selected form the group consisting of (1) mineral oils, (2) synthetic oils or mixture of synthetic oils, (3) a mixture of (1) and (2), or (4) a grease prepared from any one of (1), (2), or (3).

12. The composition of claim 11 wherein the lubricant is a mineral oil.

13. The composition of claim 11 wherein the lubricant is a grease.

14. A process for making a product of reaction suitable for use as a lubricant additive comprising (1) reacting a long chain thiodicarboxylic acid with a thionyl halide in a molar ratio of acid to halide of from about 3:1 to 1:3 at temperatures varying from 0° C. to about 120° C. for a time sufficient to obtain the corresponding sulfur-containing diacyl halide having the formula

wherein R is sulfur-containing having up to 80 carbon atoms and optionally containing oxygen or nitrogen or mixtures and X is halide selected from the group consisting of bromide, chloride, fluoride and iodide and thereafter (2) reacting in situ said diacyl halide and a hydrocarbyl phosphorodithioic acid and a hydrocarbyl phenol or thiazole or mixtures thereof at 10°–225° C., under ambient or autogenous pressure, in equimolar, less than equimolar or more than equimolar ratios of diacyl halide to said phosphorodithioic acid, the reaction times varying from about 1 to about 10 hours.

15. The process of claim 14 wherein X is chloride.

16. The process of claim 14 wherein said phenol is selected from the group consisting of monoalkyl phenols, dialkylphenols, alkoxyphenols, sulfurized alkyl phenols and sulfurized dialkyl phenols or mixtures thereof.

17. The process of claim 16 wherein said phenol is nonylphenol.

18. The process of claim 15 wherein said thiazole is selected from 2-mercaptobenzothiazole; 2,5-dimercapto-1,3,4-thiazole; 2-aminothiazole and 2-aminobenzothiazole or mixtures thereof.

19. The process of claim 18 wherein said thiazole is 2-mercaptobenzothiazole.

20. The process of claim 14 wherein said product is the reaction product of (1) 3,3'-dithiodipropionic acid and thionyl chloride and (2) the resultant diacyl chloride and bis(2-ethylhexyl) phosphorodithioic acid and 2-mercaptobenzothiazole.

21. The process of claim 14 wherein said product is the reaction product of (1) 3,3'-dithiodipropionic acid and thionyl chloride and (2) the resultant diacyl chloride and bis(2-ethylhexyl) dithiodipropionic acid and nonylphenol.

22. The process of claim 14 wherein said product is the reaction product of (1) 3,3'-thiodithiodipropionic acid and thionyl chloride and (2) the resultant diacyl chloride and bis(2-ethylhexylamido) phosphorodithioic acid and nonylphenol.

23. A lubricant additive product prepared by (1) reacting a thiodicarboxylic acid with thionyl halide in about a 3:1 to 1:3 molar ratio at temperatures varying from 0° C. to about 120° C. and (2) thereafter reacting the product of (1), a sulfur-containing diacyl halide having the formula

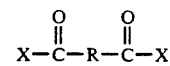

wherein R is sulfur-containing having up to 80 carbon atoms and optionally containing oxygen or nitrogen or mixtures thereof and X is halide selected from the group consisting of bromide, chloride, fluoride and iodide, in situ with a hydrocarbyl phosphorodithioic acid and phenol or thiazole at temperatures varying to reflux and recovering said desired product.

24. The additive produce of claim 25 wherein X is chloride and the dicarboxylic acid is a terminal dicarboxylic acid.

25. The additive product of claim 23 wherein said phenol is selected from the group consisting of monoalkyl phenols, dialkylphenols, alkoxyphenols, sulfurized alkyl phenols and sulfurized dialkyl phenols or mixtures thereof.

26. The additive product of claim 25 wherein said phenol is nonylphenol.

27. The additive product of claim 23 wherein said thiazole is selected from 2-mercaptobenzothiazole; 2,5-dimercapto-1,3,4-thiazole; 2-aminothiazole and 2-aminobenzothiazole or mixtures thereof.

28. The additive product of claim 27 wherein said thiazole is 2-mercaptobenzothiazole.

29. The product of claim 23 wherein the reactants are (1) 3,3'-dithiodipropionic acid and thionyl chloride and (2) the resultant diacyl chloride and bis(2-ethylhexyl) phosphorodithioic and 2-mercaptobenzothiazole.

30. The product of claim 23 wherein the reactants are (1) 3,3'-thiodithiodipropionic acid and thionyl chloride and (2) the resultant diacyl chloride and bis(2-ethylhexyl) dithiodipropionic acid and nonylphenol.

31. The product of claim 23 wherein the reactants are (1) 3,3'-thiodithiodipropionic acid and thionyl and chloride and (2) the resultant diacyl chloride and bis(2-ethylhexylamido) phosphorodithioic acid and nonylphenol.

32. A method of improving the lubricity of lubricants and reducing wear and fuel consumption in an internal combustion engine by adding to said engine a lubricating composition comprising a major amount of a lubricating oil and a minor amount of a lubricant reducing-/multifunctional additive product of reaction obtained by reacting a thiodicarboxylic acid with a thionyl halide in 3:1 to 1:3 molar ratio of acid to halide, at temperatures varying from 0° C. to 120° C. and thereafter reacting the resultant intermediate produce having the formula

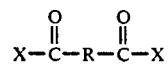

wherein R is containing having up to 80 carbon atoms and optionally containing oxygen or nitrogen or mixtures thereof and X is halide selected from the group consisting of bromide, chloride, fluoride and iodide in situ with a phosphorodithioic acid and a phenol or thiazole at temperatures varying from ambient up to reflux and recovering said desired product.

* * * * *

UNITED STATES PATENT AND TRADEMARK OFFICE
CERTIFICATE OF CORRECTION

PATENT NO. : 5,279,751

DATED : 1/18/94

INVENTOR(S) : Shi-Ming Wu and A.G. Horodysky

It is certified that error appears in the above-identified patent and that said Letters Patent is hereby corrected as shown below:

Column 7, Lines 42 & 43, After "reaction" delete "suitable"

Column 10, Line 1, delete "produce" add --product--

Signed and Sealed this

Fourteenth Day of June, 1994

*Attest:*

BRUCE LEHMAN

*Attesting Officer*  *Commissioner of Patents and Trademarks*